US006572735B1

(12) United States Patent
Wallajapet et al.

(10) Patent No.: US 6,572,735 B1
(45) Date of Patent: Jun. 3, 2003

(54) WET-FORMED COMPOSITE DEFINING LATENT VOIDS AND MACRO-CAVITIES

(75) Inventors: Palani Raj Ramaswami Wallajapet, Neenah, WI (US); Ronald Lee Edens, Appleton, WI (US); Cheryl Ann Mocadlo, New London, WI (US); Sheng-Hsin Hu, Appleton, WI (US); Dmitry Yavich, Appleton, WI (US); David Michael Kale, West Henrietta, NY (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 274 days.

(21) Appl. No.: 09/643,803

(22) Filed: Aug. 22, 2000

Related U.S. Application Data

(60) Provisional application No. 60/150,325, filed on Aug. 23, 1999.

(51) Int. Cl.$^7$ .......................... D21F 11/00; D21H 11/00; D21H 15/04; D21H 21/22
(52) U.S. Cl. ................... 162/115; 162/100; 162/109; 162/141; 162/142; 162/148; 162/149; 162/158; 162/164.1; 162/168.1
(58) Field of Search .................. 162/101, 109, 162/158, 164.1, 168.1, 183, 146, 157.6, 141, 148, 142, 149, 115, 100

(56) References Cited

U.S. PATENT DOCUMENTS

| 2,666,369 A | 1/1954 | Niks |
| 3,485,706 A | 12/1969 | Evans |
| 3,556,932 A | 1/1971 | Coscia et al. |
| 3,556,933 A | 1/1971 | Williams et al. |
| 3,700,623 A | 10/1972 | Keim |
| 3,772,076 A | 11/1973 | Keim |
| 3,821,068 A | 6/1974 | Shaw |
| 3,826,711 A | 7/1974 | Schoggen et al. |
| 3,855,158 A | 12/1974 | Petrovich et al. |
| 3,899,388 A | 8/1975 | Petrovich et al. |
| 3,981,100 A | 9/1976 | Weaver et al. |
| 3,989,586 A | 11/1976 | Bashaw et al. |
| 3,997,484 A | 12/1976 | Weaver et al. |
| 4,128,962 A | 12/1978 | Reid |
| 4,129,528 A | 12/1978 | Petrovich et al. |
| 4,147,586 A | 4/1979 | Petrovich et al. |
| 4,187,342 A | 2/1980 | Hoist et al. |
| 4,200,557 A | 4/1980 | Chatterjee et al. |
| 4,222,921 A | 9/1980 | Van Eenam |
| 4,232,674 A | 11/1980 | Melican |
| 4,260,443 A | 4/1981 | Lindsay et al. |
| 4,270,977 A | 6/1981 | Herman et al. |
| 4,295,987 A | 10/1981 | Parks |
| 4,354,901 A | 10/1982 | Kopolow |
| 4,372,312 A | 2/1983 | Fendler et al. |
| 4,414,255 A | 11/1983 | Tokuyama et al. |
| 4,500,585 A | 2/1985 | Erickson |
| 4,551,142 A | 11/1985 | Kopolow |
| 4,551,191 A | 11/1985 | Kock et al. |
| 4,675,394 A | 6/1987 | Solarek et al. |
| 4,770,657 A | 9/1988 | Ellis et al. |
| 4,851,069 A | 7/1989 | Packard et al. |
| 4,940,464 A | 7/1990 | Van Gompel et al. |
| 4,981,557 A | 1/1991 | Bjorkquist |
| 4,986,882 A | 1/1991 | Mackey et al. |
| 5,008,344 A | 4/1991 | Bjorkquist |
| 5,085,736 A | 2/1992 | Bjorkquist |
| 5,129,988 A | 7/1992 | Farrington, Jr. |
| 5,160,789 A | 11/1992 | Barcus et al. |
| 5,171,391 A | 12/1992 | Chmielwski et al. |
| 5,173,521 A | 12/1992 | Ishino |
| 5,175,046 A | 12/1992 | Nguyen |
| 5,284,703 A | 2/1994 | Everhart et al. |
| 5,399,412 A | 3/1995 | Sudall et al. |
| 5,429,686 A | 7/1995 | Chiu et al. |
| 5,443,899 A | 8/1995 | Barcus et al. |
| 5,494,554 A | 2/1996 | Edwards et al. |
| 5,529,665 A | 6/1996 | Kaun |
| 5,558,873 A | 9/1996 | Funk et al. |

(List continued on next page.)

FOREIGN PATENT DOCUMENTS

| EP | 0 359 615 A1 | 3/1990 |
| EP | 0 339 461 B1 | 1/1993 |
| EP | 0 540 041 B1 | 5/1993 |
| EP | 0 437 816 B1 | 7/1995 |
| WO | WO 86/06623 | 11/1986 |
| WO | WO 94/04751 | 3/1994 |
| WO | WO 98/24392 | 6/1998 |
| WO | WO 98/24621 | 6/1998 |
| WO | WO 98/51251 | 11/1998 |

OTHER PUBLICATIONS

TAPPI Provisional Method T 543 pm–84, "Stiffness of Paper (Gurley Type Stiffness Tester)," published by the TAPPI Press, Atlanta, Georgia, pp. 1–3.

Derwent World Patent Database abstract of Japan Carlit Co. Ltd. (JCAR): Description of JP 03–185197, "Tissue Paper Having High Tensile Strength and Water Dispersibility."

Primary Examiner—Peter Chin
(74) Attorney, Agent, or Firm—Pauley Petersen Kinne & Erickson

(57) ABSTRACT

A wet-formed composite defining latent voids and macro-cavities, the wet-formed composite having a basis weight greater than about 100 grams per square meter and a density of about 0.06 grams per cubic centimeter or more. The wet-formed composite comprises fibers and superabsorbent material, with the superabsorbent material present in an amount of about 10 dry weight percent or less, specifically about 5 dry weight percent or less, and particularly about 2 dry weight percent or less, but more than 0, based on the total dry weight of fibers and superabsorbent material present in the wet-formed composite. By virtue of the superabsorbent material having been allowed to swell and then shrink during the making of the wet-formed composite, macro-cavities are created. Densification compresses the macro-cavities. The resulting composite expands upon wetting and exhibits good absorbency properties.

18 Claims, 7 Drawing Sheets

U.S. PATENT DOCUMENTS

| | | |
|---|---|---|
| 5,607,550 A | 3/1997 | Akers |
| 5,651,862 A | 7/1997 | Anderson et al. |
| 5,667,636 A | 9/1997 | Engel et al. |
| 5,779,860 A | 7/1998 | Hollenberg et al. |
| 5,795,439 A | 8/1998 | Euripides et al. |
| 5,814,188 A | 9/1998 | Vinson et al. |
| 5,830,317 A | 11/1998 | Vinson et al. |
| 5,837,627 A | 11/1998 | Halabisky et al. |
| 5,883,231 A | 3/1999 | Achter et al. |
| 5,902,297 A | 5/1999 | Sauer |
| 5,904,672 A | 5/1999 | LeMahieu et al. |
| 5,904,675 A | 5/1999 | Laux et al. |
| 5,919,178 A | 7/1999 | Widlund |
| 5,964,973 A | 10/1999 | Heath et al. |
| 6,022,818 A | 2/2000 | Welchel et al. |

WET-FORMED COMPOSITE DEFINING LATENT VOIDS AND MACRO-CAVITIES

This application claims priority from U.S. Provisional Application No. 60/150,325 filed on Aug. 23, 1999.

BACKGROUND

People rely on absorbent products, including diapers, feminine pads, dressings for wounds, and adult incontinence articles, to participate in and enjoy their daily activities.

Absorbent products are generally manufactured by combining several components. For disposable absorbent products that are worn by a user, these components typically include a liquid-permeable topsheet; a liquid-impermeable backsheet attached to the topsheet; and an absorbent structure located between the topsheet and the backsheet. When the disposable product is worn, the liquid-permeable topsheet is positioned next to the body of the wearer and allows passage of bodily fluids into the absorbent structure. The liquid-impermeable backsheet helps prevent leakage of fluids held in the absorbent structure. Ideally the absorbent structure has three features: (1) it quickly wicks fluid into the structure; (2) it distributes fluid throughout the structure; and (3) it retains a lot of fluid.

These features can be difficult to simultaneously incorporate into the same structure. Absorption capacity increases when internal void volume in an absorbent structure increases. A higher void volume allows for containment of larger amounts of fluid. Furthermore, an absorbent structure with a higher void volume can better hold multiphasic-fluids containing solids; e.g., menses or feces.

But a higher internal void volume can mean larger pore diameters and a reduced ability to wick fluid into and throughout the absorbent structure.

What is needed is an absorbent structure, and a method of making this structure, that provide both a high absorbent capacity and the ability to wick fluid into and throughout the absorbent structure.

SUMMARY

The present invention is directed to an absorbent structure, and a method of making the absorbent structure, that satisfy this need. One method of making a wet-formed composite having latent voids and macro-cavities comprises providing fibers, a dispersion medium for the fibers, and a superabsorbent material swellable in the dispersion medium, the superaborbent material present in an amount of about 10 dry weight percent or less, specifically about 5 dry weight percent or less, and particularly about 2 dry weight percent or less, but more than 0, based on the total dry weight of fibers and superabsorbent material present in the wet-formed composite; thereafter combining the fibers, superabsorbent material, and dispersion medium; forming a wet-formed composite comprising fibers and superabsorbent material, and defining voids between the fibers, from the combination comprising fibers, superabsorbent material, and dispersion medium; providing sufficient contact time between the superabsorbent material and dispersion medium so that the superabsorbent material swells prior to drying the wet-formed composite; drying the wet-formed composite so that the superabsorbent material shrinks, thereby forming macro-cavities between the fibers; and densifying the wet-formed composite to collapse the voids and macro-cavities, thereby forming latent voids and macro-cavities within the densified wet-formed composite; wherein the densified wet-formed composite has a density of about 0.06 grams per cubic centimeter or greater and a basis weight greater than about 100 grams per square meter.

In its dry state, a wet-formed composite of the present invention is suitable for wicking fluids into and throughout the composite. When the wet-formed composite is insulted with fluid, that portion of the composite that is wetted expands as the superabsorbent material swells and latent voids and macro-cavities manifest themselves. This expansion increases internal void volume and absorbent capacity. The portion of the structure that is not yet wetted, i.e. the structure at and beyond the fluid front, remains in its unexpanded form, and therefore suitable for wicking fluids into and throughout portions of the composite increasingly remote from the initial point of fluid insult.

In another aspect, a method of the present invention comprises providing sufficient contact time between the superabsorbent material and dispersion medium before drying the wet-formed composite such that the superabsorbent material swells to at least about 50% of its maximum absorbent capacity, particularly to at least about 75% of its maximum absorbent capacity, specifically to at least about 90% of its maximum absorbent capacity, and more specifically to at least about 95% of its maximum absorbent capacity prior to drying the wet-formed composite. For papermaking processes used to make a wet-formed composite of the present invention, the dispersion medium will generally be a source of water used to operate the papermaking equipment (e.g., city/municipal water—treated or untreated at the papermaking site, papermaking process water, and the like).

In still another aspect, a method of the present invention comprises providing sufficient contact time between the superabsorbent material and dispersion medium before drying the wet-formed composite such that the superabsorbent material swells by at least about 20 grams, specifically at least about 50 grams, more specifically at least about 75 grams, particularly at least about 100 grams, more particularly at least about 150 grams, and still more particularly at least about 300 grams of dispersion medium per gram of superabsorbent material.

In yet another aspect, the amount of dispersion medium retained in the superabsorbent material after drying is suitably less than about 10% of the superabsorbent material's maximum absorbent capacity, particularly less than about 5% of the material's maximum absorbent capacity, specifically less than about 2% of the material's maximum absorbent capacity, and more specifically less than about 1% of the material's maximum absorbent capacity.

Other methods of the present invention further comprise the use of materials such as resilient fibers, synthetic fibers, wet-strength agents, dry-strength agents, other additives, and the like, in processes for preparing a wet-formed composite.

In another aspect, methods of the present invention may comprise hydroentangling the newly formed wet-formed composite (i.e., the nascent web).

Another method of the present invention involves making a disposable absorbent article, the method comprising providing a liquid-permeable topsheet, a liquid-impermeable backsheet, and a wet-formed composite defining latent voids and macro-cavities; positioning the wet-formed composite so that it will lie between the topsheet and the backsheet in the disposable absorbent article; and directly or indirectly attaching at least a portion of the topsheet to at least a portion of the backsheet.

Furthermore, the present invention encompasses combining a wet-formed composite having latent voids and macrocavities with other absorbent structures (e.g., an airlaid structure or the like) to form an absorbent core (e.g., a multi-layer absorbent core comprising the wet-laid composite and the airlaid structure). Alternatively, more than one wet-formed composite of the present invention may be combined to form a multi-layered absorbent core, with each of the plurality of wet-formed composites having the same or different materials and/or properties. Furthermore, a wet-formed composite defining latent voids and macro-cavities may be combined with films, nonwoven webs, and the like to form a multi-layered structure or laminate.

An absorbent structure having features of the present invention comprises a wet-formed composite having interbonded fibers that define latent voids and macro-cavities between the fibers; and superabsorbent material contained by the interbonded fibers, the superabsorbent material present in an amount of about 10 dry weight percent or less, specifically about 5 dry weight percent or less, and particularly about 2 dry weight percent or less, but more than 0, based on the total dry weight of fibers and superabsorbent material present in the wet-formed composite. Wet-formed composites of the present invention have a density of about 0.06 grams per cubic centimeter or greater and a basis weight greater than about 100 grams per square meter.

Wet-formed composites of the present invention may further comprise materials such as resilient fibers; synthetic fibers; wet- or dry-strength agents; other additives; and the like.

In another aspect, wet-formed composites of the present invention are characterized by certain functional properties having recited values or ranges. Examples of such properties include wet:dry cohesive strength, dry internal-cohesion, intake time, Gurley-type stiffness, wicking velocity, and increases in caliper upon wetting (these properties are discussed below).

The present invention also encompasses disposable absorbent articles comprising a wet-formed composite defining latent voids and macro-cavities.

These and other features, aspects, advantages, and versions of the present invention will become better understood with regard to the following description, appended claims, and accompanying drawings.

DRAWINGS

DESCRIPTION/REPRESENTATIVE EMBODIMENTS

Figure 1:
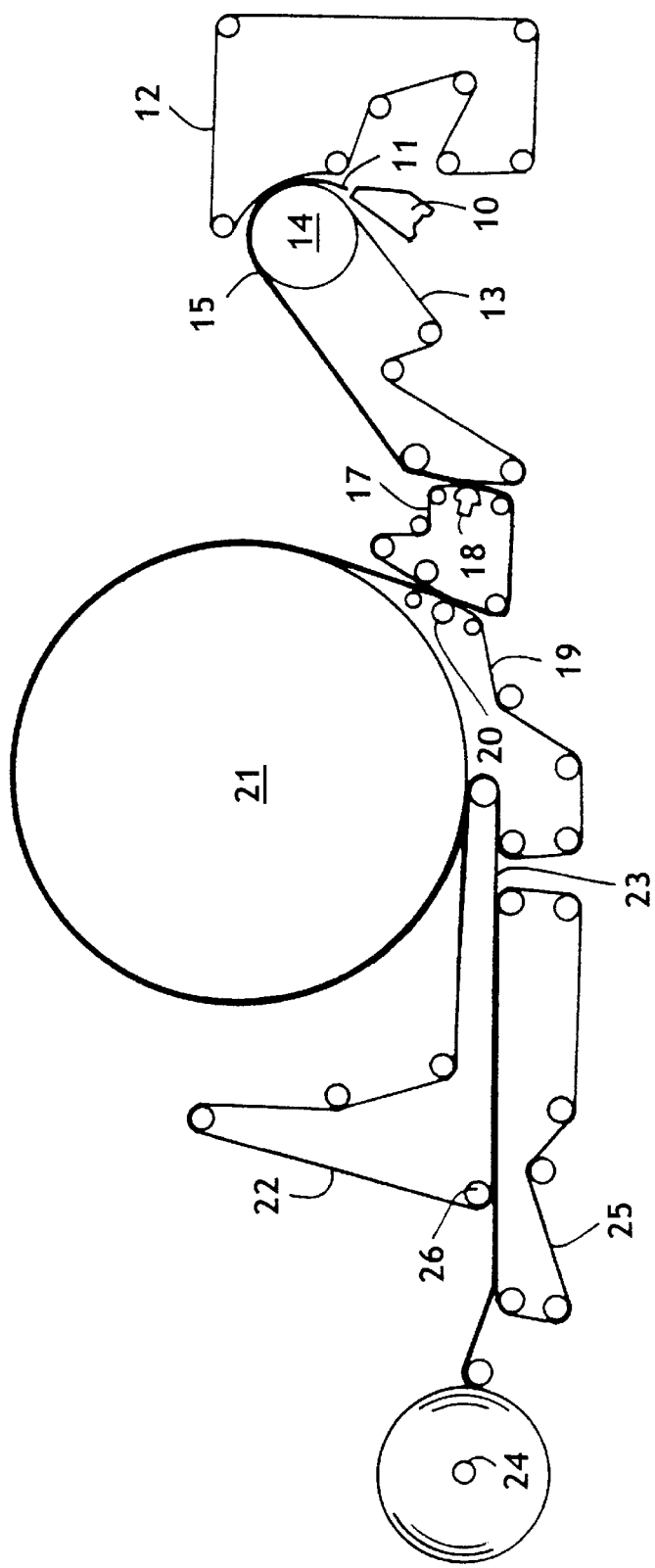
FIG. 1 depicts one version of a paper machine capable of making one or more embodiments of the present invention.

Reference now will be made to representative embodiments of the present invention, including examples set forth below. Each embodiment and example is provided by way of explanation. It will be apparent to one skilled in the art that various modifications and variations can be made without departing from the scope or spirit of the invention.

One process for preparing a wet-formed composite defining latent voids and macro-cavities comprises the steps of: providing fibers, a dispersion medium for the fibers, and a superabsorbent material swellable in the dispersion medium, the superabsorbent material present in an amount of about 10 dry weight percent or less, specifically about 5 dry weight percent or less, and particularly about 2 dry weight percent or less, but more than 0, based on the total dry weight of fibers and superabsorbent material present in the wet-formed composite; thereafter combining the fibers, superabsorbent material, and dispersion medium; forming a wet-formed composite, comprising fibers and superabsorbent material, and defining voids between the fibers, from the combination of fibers, superabsorbent material, and dispersion medium; providing sufficient contact time between the superabsorbent material and dispersion medium so that the superabsorbent material swells prior to drying the wet-formed composite; drying the wet-formed composite so that the superabsorbent material shrinks, thereby forming macro-cavities between the fibers; and densifying the wet-formed composite to collapse the voids and macro-cavities, thereby forming latent voids and macro-cavities within the densified wet-formed composite; wherein the densified wet-formed composite has a density of about 0.06 grams per cubic centimeter or greater and a basis weight greater than about 100 grams per square meter.

Other versions of a process of the present invention are described herein. Presently representative materials useful for the present invention are discussed.

Fibers suitable for use in the present invention are known to those skilled in the art. Any fiber from which a wet-formed composite can be formed is believed suitable for use. Examples of fibers suitable for use in the present invention include, cellulosic fibers such as wood pulp, cotton linters, cotton fibers and the like; synthetic polymeric fibers such as polyolefin fibers, polyamide fibers, polyester fibers, polyvinyl alcohol fibers, polyvinyl acetate fibers, synthetic polyolefin wood pulp fibers, and the like; as well as regenerated cellulose fibers such as rayon and cellulose acetate microfibers. Mixtures of various fiber types are also suitable for use. For example, a mixture of cellulosic fibers and synthetic polymeric fibers may be used. As a general rule, the fibers will have a length-to-diameter ratio of at least about 2:1, preferably of at least about 5:1. As used herein, "diameter" refers to a true diameter if generally circular fibers are used or to a maximum transverse cross-sectional dimension if non-circular, e.g., ribbon-like, fibers are used. The fibers will generally have a length of from about 0.5 millimeter to about 25 millimeters, preferably from about 1 millimeter to about 6 millimeters. Fiber diameters will generally be from about 0.001 millimeter to about 1.0 millimeter, preferably from about 0.005 millimeter to about 0.01 millimeter. For reasons such as economy, availability, physical properties, and ease of handling, cellulosic wood pulp fibers are suitable for use in the present invention.

Other fibers useful for purposes of the present invention are resilient fibers that include high-yield pulp fibers (further discussed below), flax, milkweed, abaca, hemp, cotton, or any of the like that are naturally resilient or any wood pulp fibers that are chemically or physically modified, e.g. crosslinked or curled, that have the capability to recover after deformation from preparing the composite, as opposed to non-resilient fibers which remain deformed and do not recover after preparing the composite.

As used herein, "high yield pulp fibers" are those papermaking fibers produced by pulping processes providing a yield of about 65 percent or greater, more specifically about 75 percent or greater, and still more specifically from about 75 to about 95 percent. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulphite pulps, and high yield kraft pulps, all of which leave the resulting fibers with higher levels of lignin. Suitable high-yield pulp fibers are generally characterized as being comprised of comparatively whole, relatively undamaged tracheids, high freeness (over 250 CSF), and low fines content (less than 25 percent by the Britt jar test).

The amount of resilient fibers in the wet-formed composite can be at least about 10 dry weight percent or greater, more specifically about 30 dry weight percent or greater, still more specifically about 50 dry weight percent or greater, particularly about 70 dry weight percent or greater, and up to 100 dry weight percent based on the total dry weight of fibers present in the wet-formed composite. For layered wet-formed composites, i.e. composites made using a stratified or multi-layered headbox, these same amounts can be applied to one or more of the individual layers. Individual layers may have the same or different amounts of resilient fibers.

As used herein, the term "superabsorbent material" and similar terms refer to a water-swellable, generally water-insoluble material capable of absorbing at least about 20, specifically at least about 50, more specifically at least about 75, particularly at least about 100, more particularly at least about 150 times, and still more particularly at least about 300 times or more its weight in water (or other dispersion medium). The superabsorbent material may be formed from organic material which may include natural materials such as agar, pectin, and guar gum, as well as synthetic materials such as synthetic hydrogel polymers. Synthetic hydrogel polymers include, for example, carboxymethylcellulose, alkali metal salts of polyacrylic acid and its copolymers, polyacrylamides, polyvinyl alcohol, ethylene maleic anhydride copolymers, polyvinyl ethers, hydroxypropylcellulose, hydroxypropyl acrylate, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, and isobutylene maleic anhydride copolymers and mixtures thereof. The hydrogel polymers are suitably lightly crosslinked to render the material substantially water-insoluble. Crosslinking may, for example, be by irradiation or by covalent, ionic, Van der Waals, or hydrogen bonding. Suitable materials are available from various commercial vendors, such as the Dow Chemical Company, Stockhausen Inc., and Chemtall Inc. The noncellulosic, synthetic hydrogel polymers are suitable for use in the present invention.

The superabsorbent material may be in the form of discrete particles, agglomerated particles, fibers, spheres or the like. When in the form of discrete particles, the particles will generally have a maximum cross-sectional dimension of from about 10 micrometers to about 2000 micrometers, specifically of from about 50 micrometers to about 1000 micrometers, and more specifically from about 100 micrometers to 500 micrometers.

The superabsorbent material present in the wet-formed composites is swellable in the dispersion medium. As used herein, a superabsorbent material will be considered to be swellable in the dispersion medium when the superabsorbent material can absorb at least about 20 times, specifically at least about 50 times, more specifically at least about 75 times, particularly at least about 100 times, more particularly at least about 150 times, and still more particularly at least about 300 times or more its weight in the dispersion medium when the superabsorbent material is dispersed in an excess of the dispersion medium for a period of one hour.

A variety of materials may be suitable for use as the dispersion medium. Exemplary of dispersion mediums are water, other aqueous materials, and the like. For reasons such as availability and economy, water is a suitable dispersion medium. For papermaking processes used to make wet-formed composites of the present invention, the dispersion medium may be city/municipal water, papermaking process water, treated water, or some other source of water used in operating the papermaking equipment (e.g., the stock preparation system; discussed in more detail below).

Prior to the fiber/dispersion medium slurry (and other elements that may be present in the slurry; e.g. superabsorbent material and/or other additives as detailed herein) being conducted to a forming surface to form a nascent web (i.e., a newly formed wet-formed composite), the fibers are present in the dispersion medium in an amount of from about 0.005 to about 3.0 weight percent, specifically of from about 0.01 to about 2.0 weight percent and, particularly from about 0.01 to about 1.0 weight percent, based on total weight of the fibers and dispersion medium (known to those skilled in the art as "consistency"). The dispersion medium may contain other additives known to those skilled in the art of papermaking. Other suitable additives include, without limitation, binders, viscosity modifiers, adhesives, dry-strength agents, wet-strength agents (discussed in more detail below), pH control additives, flocculants, and the like, provided they do not deleteriously affect the formation or desired performance properties of the wet-formed composites. Additives may also be combined with the wet-formed composite after the composite has been formed (e.g., by spraying, coating, printing, or the like).

There are a number of materials commonly used in the paper industry to impart wet strength to paper and board that are applicable to this invention. These materials are known in the art as wet-strength agents and are commercially available from a wide variety of sources. Any material that when added to a wet-formed composite increases the wet cohesive strength:dry cohesive strength ratio in excess of 0.05 will, for purposes of this invention, be termed a wet-strength agent. Typically these materials are termed either as permanent wet-strength agents or as "temporary" wet-strength agents. For the purposes of differentiating permanent from temporary wet strength, permanent will be defined as those resins which, when incorporated into wet-formed composites, will provide a composite that retains more than 50% of its original wet-cohesive strength after exposure to water for a period of at least five minutes. Temporary wet-strength agents are those that show less than 50% of their original wet cohesive strength after exposure to water for five minutes. Both classes of material find application in the present invention.

The amount of wet-strength agent added to the pulp fibers can be at least about 0.1 dry weight percent or greater, specifically at least about 0.2 dry weight percent or greater, particularly at least about 0.5 dry weight percent or greater, more particularly from about 0.2 to about 1 dry weight percent, and still more particularly from about 0.1 to about 3 dry weight percent based on the dry weight of the fibers.

The permanent wet-strength agents that are of utility in the present invention are typically water soluble, cationic, oligomeric or polymeric resins that are capable of either crosslinking with themselves (homocrosslinking) or with the cellulose or other constituent of the fiber. The most widely used materials for this purpose are the class of polymer known as polyamide-polyamine-epichlorohydrin (PAE) type resins. These materials have been described in patents issued to Keim (U.S. Pat. Nos. 3,700,623 and 3,772,076) and are sold by Hercules, Inc., Wilmington, Del., as Kymene 557H. Related materials are marketed by Henkel Chemical Co., Charlotte, N.C. and Georgia-Pacific Resins, Inc., Atlanta, Ga.

Polyamide-epichlorohydrin resins are also useful as bonding resins in this invention. Materials developed by Monsanto and marketed under the Santo Res label are base-activated polyamide-epichlorohydrin resins that can be used in the present invention. These materials are described in patents issued to Petrovich (U.S. Pat. Nos. 3,855,158; 3,899,388; 4,129,528 and 4,147,586) and van Eenam (U.S. Pat. No. 4,222,921). Although they are not as commonly used in consumer products, polyethylenimine resins are also suitable for immobilizing the bond points in the products of this invention. Other classes of permanent-type wet-strength agents are exemplified by the aminoplast resins obtained by reaction of formaldehyde with melamine or urea.

The temporary wet-strength resins that can be used in connection with this invention include, but are not limited to, those resins that have been developed by American Cyanamid and are marketed under the name Parez 631 NC (now available from Cytec Industries, West Paterson, N.J.). This and similar resins are described in U.S. Pat. No. 3,556,932 to Coscia et al. and U.S. Pat. No. 3,556,933 to Williams et al. Other temporary wet-strength agents that should find application in this invention include modified starches such as those available from National Starch and marketed as Co-Bond 1000. It is believed that these and related starches are covered by U.S. Pat. No. 4,675,394 to Solarek et al. Derivatized dialdehyde starches, such as described in Japanese Kokai Tokkyo Koho JP 03,185,197, should also find application as useful materials for providing temporary wet strength. It is also expected that other temporary wet-strength materials such as those described in U.S. Pat. Nos. 4,981,557, 5,008,344, and 5,085,736 to Bjorkquist would be of use in this invention. With respect to the classes and the types of wet-strength resins listed, it should be understood that this listing is simply to provide examples and that this is neither meant to exclude other types of wet-strength resins, nor is it meant to limit the scope of this invention.

Although wet-strength agents as described above find particular advantage for use in connection with this invention, other types of bonding agents can also be used. They can be applied at the wet end or applied by spraying or printing, etc. after the wet-formed composite is formed or after it is dried.

As used herein, the wet:dry ratio is the ratio of the wet cohesive strength divided by the dry cohesive strength. Cohesive strength, as used herein, means z-directional bonding strength. Cohesive strength is measured by mounting a sample between sample holders on a tensile tester. Two-sided adhesive tape is used on the surface of each holder so that the opposing faces of the sample are each affixed to a sample-holder surface. The tensional forces act on opposing faces of the sample, thus providing a measure of z-directional bonding strength. Wet-formed composites of the present invention that comprise a wet-strength agent will have a wet:dry ratio of about 0.05 or greater, more specifically about 0.1 or greater, still more specifically about 0.15 or greater, particularly about 0.3 or greater, still more particularly about 0.5 or greater, and still more particularly about 0.7 or greater.

As used herein, the terms "wet-formed," "wet-laid," and the like refer to composites that are formed from a process in which fibers are dispersed in a liquid dispersion medium to form a slurry. The slurry is deposited on a forming surface to form the composite by removal of at least a portion of the dispersion medium. Those skilled in the art are familiar with such processes.

FIG. 1 depicts one version of a paper machine capable of making an embodiment of the invention. For simplicity, the various tensioning rolls schematically used to define the several fabric runs are shown but not numbered. It will be appreciated that variations from the apparatus and method illustrated in FIG. 1 can be made without departing from the scope of the invention.

A slurry of fibers and the dispersion medium is prepared in a stock preparation system (not shown). Such systems are known to persons of ordinary skill. The superabsorbent material is combined with the slurry of fibers so that the superabsorbent material absorbs at least about 20 times, specifically at least about 50 times, more specifically at least about 75 times, particularly at least about 100 times, more particularly at least about 150 times, and still more particularly at least about 300 times or more its weight in the dispersion medium before the wet-formed composite is dried. Suitably the superabsorbent material swells to the above-recited amounts before the wet-formed composite is formed. The superabsorbent material may be added at a location in the stock preparation system so that the superabsorbent material is distributed relatively uniformly throughout the slurry prior to forming a wet-formed composite. The superabsorbent material may also be preswollen in a dispersion medium, suitably the same or similar dispersion medium as is used to prepare the fiber slurry, before being added to the fiber slurry. If a multi-layer or stratified headbox is used, differing amounts, chemistries, types, or shapes of superabsorbent material may be added to each stock preparation system used to feed a given layer in the headbox.

The maximum amount of dispersion medium which the superabsorbent material absorbs, after being combined with the slurry of fibers and dispersion medium until the point of drying, can be experimentally determined by comparing the weight of the wet composite, prior to drying, to the weight of the dry composite after drying. The weight of dispersion medium removed by drying generally represents the maximum amount of dispersion medium capable of being absorbed by the superabsorbent material. Such a calculation assumes all dispersion medium removed by drying was present in the superabsorbent material. The actual amount of dispersion medium held in the superabsorbent material prior to drying is less than the experimentally-determined maximum amount (some of the dispersion medium may be in or between fibers but not in the superabsorbent material) and depends on the length of exposure of the superabsorbent material to the dispersion medium, as well as the relative amounts of fiber and superabsorbent material in the wet-formed composites.

Returning to FIG. 1, the diagram depicts a twin-wire former having a layered papermaking headbox 10 which injects or deposits a stream 11 of the fiber/dispersion medium/superabsorbent material combination onto the forming fabric 13 which serves to support and carry the newly-formed wet-formed composite (i.e., the nascent web) in the process as the composite is partially dewatered to a consistency of about 10 dry weight percent. Additional dewatering of the wet-formed composite can be carried out, such as by vacuum suction, while the composite is supported by the forming fabric.

A person of ordinary skill will recognize that one or all layers of the stratified headbox may be devoted to preparing a wet-formed composite of the present invention. Furthermore, each layer may contain differing amounts, chemistries, types, or shapes of superabsorbent material or resilient fibers, as well as differing amounts, chemistries, or types of wet-strength agents or other additives, so that each layer has different performance characteristics. Alternatively, a single-layer headbox may be employed to make wet-formed composites encompassed by the present invention.

The wet-formed composite is then transferred from the forming fabric to a transfer fabric 17. The transfer fabric may travel at a slower speed than the forming fabric in order to impart increased stretch into the composite. Transfer is suitably carried out with the assistance of a vacuum shoe 18 such that the forming fabric and the transfer fabric converge and diverge simultaneously at the leading edge of the vacuum slot as described in U.S. Pat. No. 5,667,636 to Engel et al., which is hereby incorporated by reference in a manner consistent herewith.

The wet-formed composite is then transferred from the transfer fabric to the through-air-drying fabric 19 with the aid of a vacuum transfer roll 20 or a vacuum transfer shoe, optionally again using a fixed-gap transfer as previously described. Alternatively, the wet-formed composite may be transferred directly from the forming fabric to the through-air-drying fabric. The through-air-drying fabric can be traveling at about the same speed or a different speed relative to the transfer fabric or forming fabric. If desired, the through-air-drying fabric can be run at a slower speed to further enhance stretch. Transfer is suitably carried out with vacuum assistance to ensure deformation of the sheet to conform to the through-air-drying fabric, thus yielding desired bulk and appearance. Suitable through-air-drying fabrics include those having a three-dimensional contour as described in U.S. Pat. No. 5,429,686 issued Jul. 4, 1995 to Chiu et al. entitled "Apparatus For Making Soft Tissue Products", which is hereby incorporated by reference.

The level of vacuum used for the wet-formed composite transfers can be from about 3 to about 15 inches of mercury (75 to about 380 millimeters of mercury), suitably about 5 inches (125 millimeters) of mercury. The vacuum shoe (negative pressure) can be supplemented or replaced by the use of positive pressure from the opposite side of the wet-formed composite to blow the wet-formed composite onto the next fabric in addition to or as a replacement for sucking it onto the next fabric with vacuum. Also, a vacuum roll or rolls can be used to replace the vacuum shoe(s).

While supported by the through-air-drying fabric, the wet-formed composite is final dried to a consistency of about 80 percent or greater by the through-air-dryer 21 and thereafter transferred to a carrier fabric 22. The dried composite 23 is transported to the reel 24 using carrier fabric 22 and an optional carrier fabric 25. An optional pressurized turning roll 26 can be used to facilitate transfer of the wet-formed composite from carrier fabric 22 to fabric 25. Suitable carrier fabrics for this purpose are Albany International 84M or 94M and Asten 959 or 937, all of which are relatively smooth fabrics having a fine pattern.

Densification of the wet-formed composite can be carried out by a number of methods. It is well known that passing sheets through one or more rollers or nips will help compress and smooth the surfaces of materials. The equipment used to do this is termed a calender or supercalender. The effect of calendering on composites of the present invention depends upon the temperature, the pressure applied, and the duration of the pressure. For purposes herein, calendering can be carried out at either at ambient or elevated temperatures. Suitable calendering pressures can be from about 50 to about 1400 pounds-force per linear inch (pli). Suitable temperatures can be from about 20° C. to about 240° C. The duration of calendering can be varied in conjunction with the nip pressure to produce the desired caliper for the sheet.

In addition to calendering or supercalendering, the wet-formed composites can be densified using flat platten presses or fabric nips used to smooth and compact multi-wiper products as disclosed in U.S. Pat. No. 5,399,412 to Sudall et al. In this instance, the multi-ply wiper is carried on fabrics through a nip and the overall caliper of the multi-ply product is reduced. A similar process can be used to produce composites of the present invention. By inducing a pattern in the fabric or fabrics, the resulting composite could have areas that are highly compressed and areas that are less compressed. The response of the resulting composites to fluids would result in expansion of the composite, more or less uniformly, for the entire composite.

In some versions of the invention, the nascent web of fibers (i.e., the newly-formed wet-formed composite) is hydroentangled using equipment known to those skilled in the art. For example, U.S. Pat. No. 6,022,818, entitled "Hydroentangled Nonwoven Composites," which is hereby incorporated by reference in a manner consistent with the present application, describes one version of a hydroentangling process (see, e.g., col. 8, lines 4–64 for one description of such a process). As described in the Examples below, hydroentangling affects cohesion and stiffness of the resulting composite. Generally, increasing hydroentangling of the fibers in a nascent web increases cohesive strength and decreases stiffness in the dried, wet-formed composite. Furthermore, increasing hydroentangling of the nascent web typically increases the dryness of the web just after the hydroentangling operation. Accordingly, positioning a hydroentangling unit operation before the selected drying operation (whether it be a through-air-drying operation; a Yankee dryer; a series of drying cans; an irradiative drying operation; some combination of these; or some other operation used to increase the percent solids of the web—i.e., reduce the amount of moisture in the web) would be expected to decrease the amount of energy required by the selected drying operation to achieve a given percent solids in the web after the drying operation.

Figure 2:
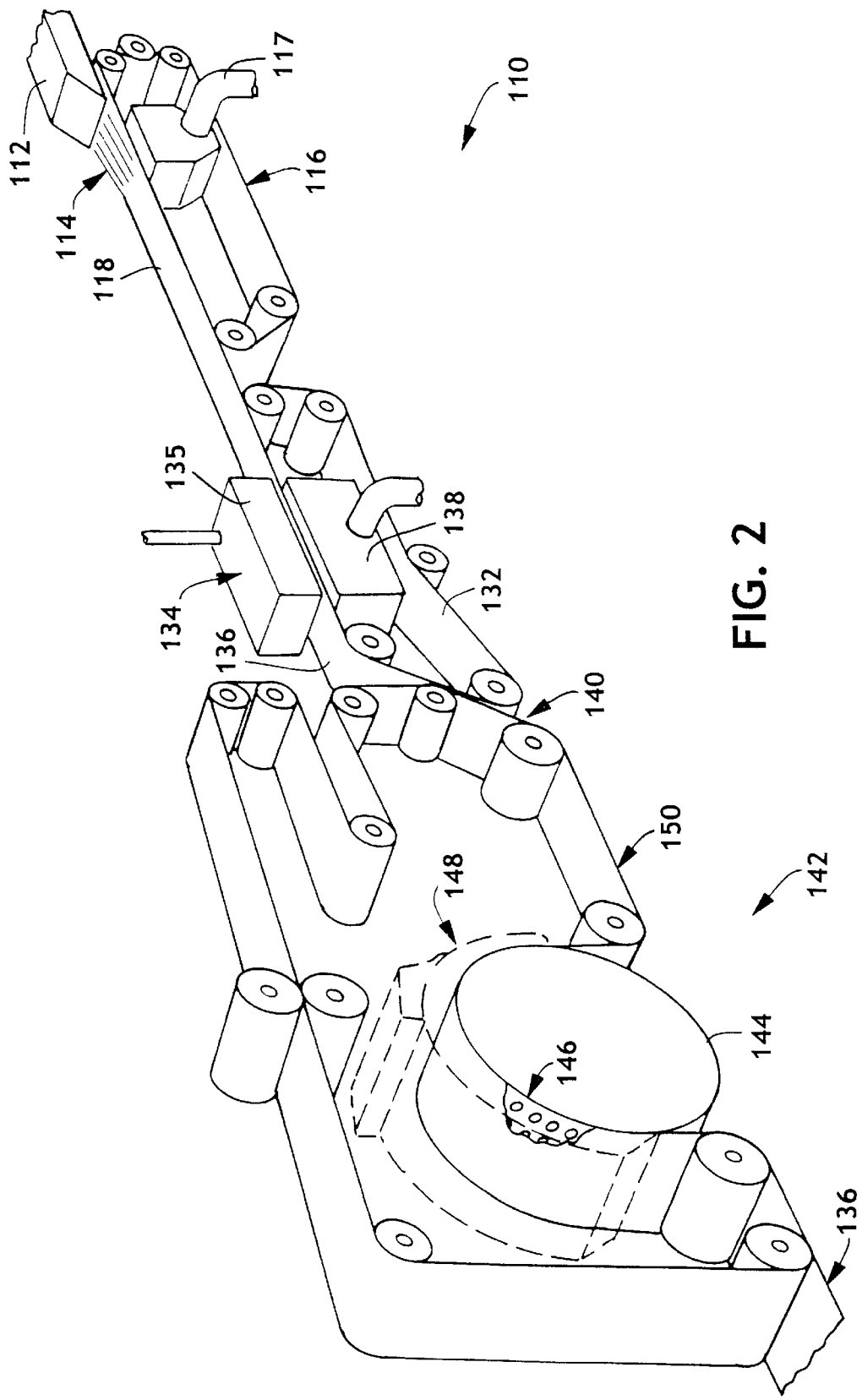
FIG. 2 depicts one version of a paper machine capable of making one or more embodiments of the present invention.

The schematic in FIG. 2 shows one version of a process comprising an example of hydraulic entangling equipment. As discussed above, a slurry comprising fibers and the selected dispersion medium is prepared in a stock preparation system (not shown). The slurry is supplied to a headbox 112 and is deposited via a sluice 114 onto a forming surface 116. One example of a forming surface is a Formtech 90BH Flat Warp 90×50 mesh, single-layer weave, available from Albany International of Portland, Tenn. The warp strands are 0.17 mm polyester. The shute strands are 0.25 mm polyamide. The average caliper is 0.018 inch; Air Permeability is 525 cfm (cubic feet per minute); and the open area is 20 percent. The slurry may be diluted to any consistency that is typically used in a conventional papermaking process. For example, the slurry may contain from about 0.05 to about 0.5 percent by weight pulp fibers in water to form a slurry. The slurry is deposited on the forming surface 116 and a vacuum assist 117 is used to pull water out of the deposited fibers thereby creating a newly-formed wet-formed composite 118 (i.e., a nascent web of fibers).

The wet-formed composite 118 is then directed to a foraminous entangling surface 132 of a hydraulic entangling machine. The wet-formed composite 118 passes under one or more hydraulic entangling manifolds 134 and is treated with jets of fluid to entangle the pulp fibers with one another, thereby forming a hydroentangled wet-formed composite 136. Alternatively, hydraulic entangling may take place while the wet-formed composite 118 is on the same foraminous screen (i.e., mesh fabric) on which wet-laying took place. The present invention also contemplates rehydrating a dried, wet-formed composite to a specified consistency and then subjecting the rehydrated wet-formed composite to hydraulic entangling. The hydraulic entangling may take place while the wet-formed composite 118 is highly saturated with water. For example, the wet-formed composite 118 may contain up to about 90 percent by weight water just before hydraulic entangling.

The hydraulic entangling may be accomplished by utilizing hydraulic entangling equipment such as may be found in, for example, U.S. Pat. No. 3,485,706 to Evans and U.S. Pat. No. 5,284,703 to Everhardt et al., both of which are incorporated herein by reference in their entirety and in a manner consistent herewith. The hydraulic entangling may be carried out with any appropriate working fluid such as, for example, water. The working fluid flows through one or more manifolds 135 which evenly distribute the fluid to a series of individual holes or orifices. The holes or orifices may be from about 0.003 to about 0.015 inches (0.076 to 0.38 millimeters) in diameter. For example, the invention may be practiced utilizing a manifold produced by Honeycomb Systems, Inc. of Biddeford, Me. containing a single row of aligned holes (30 holes per inch/12 holes per centimeter) with each hole having a diameter of 0.007 inches (0.18 millimeters). In the process used to form the examples of the present invention, three manifolds of the type just described were aligned in sequence across the traveling layer 118. In the hydraulic entangling process the working fluid passes through the orifices at a pressure ranging from about 200 to about 2000 pounds per square inch guage (psig) (about 1379 kilopascals to about 13,790 kilopascals). The number of manifolds 135 and the pressure within each manifold will affect the degree of integration of the fibers.

The fluid impacts the wet-formed composite 118 which is supported by a foraminous surface 132 which may be, for example, a single plane mesh wire having a mesh size of from about 40×40 strands per inch (15.7×15.7 strands per centimeter) to about 100×100 strands per inch (39.4×39.4 strands per centimeter). The foraminous surface 132 may also be a multi-ply mesh having a mesh size from about 50×50 to about 200×200 strands per inch (19.7×19.7 to about 78.7×78.7 strands per centimeter). One example of a foraminous surface used in the hydraulic entangling operation may be obtained from Albany International of Portland, Tenn. The wire may be described as a 12-C Flat Warp 14×15 mesh, single-layer weave. The warp strands are 0.88×0.57 mm polyester. The shute strands are 0.76 mm polyamide. The average caliper is 0.0515 inch; air permeability is 770 cfm (cubic feet per minute); and the open area is 28 percent.

As is typical in many water-jet treatment processes, vacuum slots 138 may be located directly beneath the hydro-needling manifolds 135 or beneath the foraminous entangling surface 132 downstream of the manifolds 135 so that excess water can be withdrawn from the entangled wet-formed composite 136.

After the fluid jet treatment, the entangled wet-formed composite 136 may be transferred to a non-compressive drying operation or a compressive drying operation such as steam cans (not shown). A differential speed pick-up roll 140 may be used to transfer the material from the hydraulic needling belt to a non-compressive drying operation. Alternatively, conventional vacuum-type pick-ups and transfer fabrics may be used. If desired, the composite fabric may be wet creped before being transferred to the drying operation. Non-compressive drying of the web may be accomplished utilizing a conventional rotary drum through-air dryer 142. The through-air dryer 142 maybe an outer rotatable cylinder 144 with perforations 146 in combination with an outer hood 148 for receiving hot air blown through the perforations 146. A through-dryer belt 150 carries the composite fabric 136 over the upper portion of the through-dryer outer cylinder 144. The heated air forced through the perforations 146 in the outer cylinder 144 of the through-dryer 142 removes water from the entangled wet-formed composite 136. The temperature of the air forced through the composite fabric 136 by the through-dryer 142 may range from about 93 degrees Celsius (C.) to about 260 degrees C. (200 degrees F. to about 500 degrees F.). Other useful through-drying methods and apparatus may be found in, for example, U.S. Pat. Nos. 2,666,369 and 3,821,068, both of which are incorporated herein by reference in their entirety and in a manner consistent herewith.

As discussed above, finishing steps and/or post-treatment processes may be used to impart selected properties to the entangled wet-formed composite 136. For example, the composite may be pressed by calendar rolls, and/or creped or brushed to provide a uniform exterior appearance and/or certain tactile properties. Alternatively, and/or additionally, chemical post-treatments such as surfactants, adhesives or dyes may be added to the entangled wet-formed composite.

The dried wet-formed composites of the present invention comprise fibers in an amount of about 90 dry weight percent or greater, specifically about 95 dry weight percent or greater, and particularly of about 98 dry weight percent or greater, but less than 100 dry weight percent, based on total dry weight of the fibers and superabsorbent material present in the wet-formed composite. The fibers are interbonded, either through fiber-fiber interactions or by the effect of one or more additives such as a wet-strength agent, and these bonds may be covalent, ionic, of the Van der Waals type, of the hydrogen-bond type, or some combination of these.

The superabsorbent material is present in an amount of about 10 dry weight percent or less, specifically of about 5 dry weight percent or less, and particularly of about 2 dry weight percent or less, but more than 0, based on the total dry weight of the fibers and superabsorbent material present in the wet-formed composite. The amount of superabsorbent material is selected in part so that the wet-formed composite comprises interbonded fibers defining macro-cavities between the fibers after the drying step, but does not significantly reduce production capacity by virtue of the amount of water that must be removed from the swollen superabsorbent material during the drying step.

Suitably the superabsorbent material swells to at least about 50% of its maximum absorbent capacity, particularly to at least about 75% of its maximum absorbent capacity, specifically to at least about 90% of its maximum absorbent capacity, and more specifically to at least about 95% of its maximum absorbent capacity prior to the step in which the wet-formed composite is dried. For purposes of this application, "maximum absorbent capacity" means the amount of dispersion medium (e.g., city/municipal water; papermaking process water; or other liquid) absorbed and/or adsorbed by the superabsorbent material when the superabsorbent material is placed in an excess of the dispersion medium for a time sufficient for the superabsorbent material to swell to its maximum capacity (i.e., it is no longer absorbing and/or adsorbing dispersion medium), which generally will be achieved after one hour at room temperature (i.e., from about 68 to about 72 degrees Fahrenheit). Many superabsorbent materials will achieve their maximum absorbent capacity in a time less than one hour. Thus a superabsorbent material with a maximum absorbent capacity of 150 grams of dispersion medium per gram of superabsorbent material is fully swollen and is at 100% of the material's absorbent capacity when 1 gram of the superabsorbent material has absorbed/adsorbed 150 grams of dispersion medium. It should be understood that other measures of maximum absorbent capacity may be used, with the invention encompassing wet-formed composites comprising a superabsorbent material that is appreciably swollen (i.e., the superabsorbent material is at about 50% to about 75% of its maximum absorbent capacity), particularly substantially swollen (i.e., the superabsorbent material is at about 75% to about 95% of its maximum absorbent capacity), and more particularly fully swollen before the wet-formed composite is dried (i.e., the superabsorbent material is at about 95% to about 100% of its absorbent capacity). Increasing the degree of swelling prior to the drying step should increase the size of the latent macrocavities because a more fully-swollen superabsorbent should occupy more volume in the wet-formed composite prior to drying. But a more fully-swollen superabsorbent material may mean that additional water must be driven off during drying (depending on the degree to which the fully-swollen superabsorbent material is subsequently shrunk). The amount of dispersion medium retained in the superabsorbent material after drying is suitably less than about 10% of the material's maximum absorbent capacity, particularly less than about 5% of the material's maximum absorbent capacity, specifically less than about 2% of the material's maximum absorbent capacity, and more specifically less than about 1% of the material's maximum absorbent capacity.

Dried wet-formed composites of the present invention have a basis weight less than about 600 grams per square meter, specifically less than about 250 grams per square meter, more specifically less than about 150 grams per square meter, particularly between about 150 and about 250 grams per square meter, but more than about 100 grams per square meter.

After the dried wet-formed composite has been densified, composites of the present invention have a density of about 0.06 grams per cubic centimeter or greater, specifically of about 0.12 grams per cubic centimeter or greater, more specifically of about 0.15 grams per cubic centimeter or greater, and particularly from about 0.12 to about 0.15 grams per cubic centimeter, but less than about 0.5 grams per cubic centimeter. Density is selected in part so that the internal pore structure of the dried, wet-formed composite is suitable for wicking and distributing fluid throughout the composite. Density may also be selected so that the dried, wet-formed composite helps impart softness and thinness to the product in which the wet-formed composite is incorporated.

When fully wetted or saturated with dispersion medium (e.g., city/municipal water), the caliper of the wet-formed composite of this invention can increase by about 50 percent or greater, specifically by about 100 percent or greater, more specifically by about 200 percent or greater, still more specifically by about 400 percent or greater, particularly from about 400 percent to about 600 percent, and more particularly by about 600 percent or greater.

Dried wet-formed composites of the present invention are suitable for incorporation into a number of types of absorbent articles. For example, wet-formed composites defining latent voids and macrocavities may be used as, or part of, an absorbent core in articles such as feminine care articles, dressings for wounds, diapers, adult-incontinence articles, and the like. Furthermore, the present invention contemplates combining a wet-formed composite having latent voids and macro-cavities with other absorbent structures (e.g., an airlaid structure or the like) to form an absorbent core (e.g., a multi-layer absorbent core comprising the wet-laid composite and the airlaid structure). Alternatively, more than one wet-formed composite may be combined to form a multi-layered absorbent core, with each of the plurality of wet-formed composites having the same or different properties. Furthermore, a wet-formed composite defining latent voids and macro-cavities may be combined with films, nonwoven webs, and the like.

Examples of disposable absorbent articles or absorbent composites into which wet-formed composites of the present invention may be incorporated include, but are not limited to: U.S. Pat. No. 4,940,464, entitled "Disposable Incontinence Garment or Training Pant,"; U.S. Pat. No. 5,904,675, entitled "Absorbent Article with Improved Elastic Margins and Containment System,"; U.S. Pat. No. 5,904,672, entitled "Absorbent Article having Improved Waist Region Dryness and Method of Manufacture,"; U.S. Pat. No. 5,902,297, entitled "Absorbent Article Having a Collection Conduit,"; U.S. Pat. No. 4,372,312, entitled "Absorbent Pad Including Microfibrous Web"; and U.S. Pat. No. 4,770,657, entitled "Three-Dimensional Shaped Feminine Pad with Absorbent in the Elasticized Edges"; each of which is hereby incorporated by reference in its entirety in a manner consistent herewith.

These variations are given only as examples. It should be understood, however, that the invention encompasses use of wet-formed composites defining latent voids and macrocavities in other combinations and in other absorbent articles or composites.

To illustrate the invention, representative embodiments of wet-formed composites of the present invention were made and tested as discussed below.

EXAMPLE 1

Some embodiments of the wet-formed composites were made using a Model Number Series 9000 computerized handsheet former, manufactured by M/K Systems, Danvers, Mass. The general procedure for making these embodiments was as follows. First, the selected amount of fiber was dispersed in water along with the selected amount of Kymene 557LX, available from Hercules Inc., a business having offices in Wilmington, Del., to form a slurry of fibers. Next the slurry of fibers was added to the mold of the handsheet former. The slurry was agitated by dispersing air into the slurry for about 60 seconds. The selected amount of superabsorbent material, after having been placed in distilled water (approximately 1000 g distilled water for 1 g of superabsorbent material) for about 15 to 30 minutes, was then added to the slurry in the mold and agitation with air continued for about 60 seconds. The agitation was then stopped, and the slurry/superabsorbent material combination allowed to stand for about 5 seconds. Water was drained from the mold to form a wet-formed composite on the screen. Two blotters were placed on the composite and a roller was used to contact the composite with the blotters. The wet-formed composite was then picked up and placed onto a stainless steel wire screen and dried in a convection oven at 105 degrees Celsius. After drying, the sheet was densified to achieve the desired caliper for a given basis weight. The densifying device used for these examples was a Model 3912 hydraulic press available from Fred S. Carver Hydraulic Equipment Inc., a business having offices in Menomonee Falls, Wis. Dried handsheets, or samples cut from rolls (see Examples 8 and 9 below), were placed on a bottom plate. The device was then activated so that the upper plate was hydraulically pressed against the sample and lower plate. The applied pressure typically was about 16,000 pounds per square inch.

EXAMPLE 2

Figure 3:
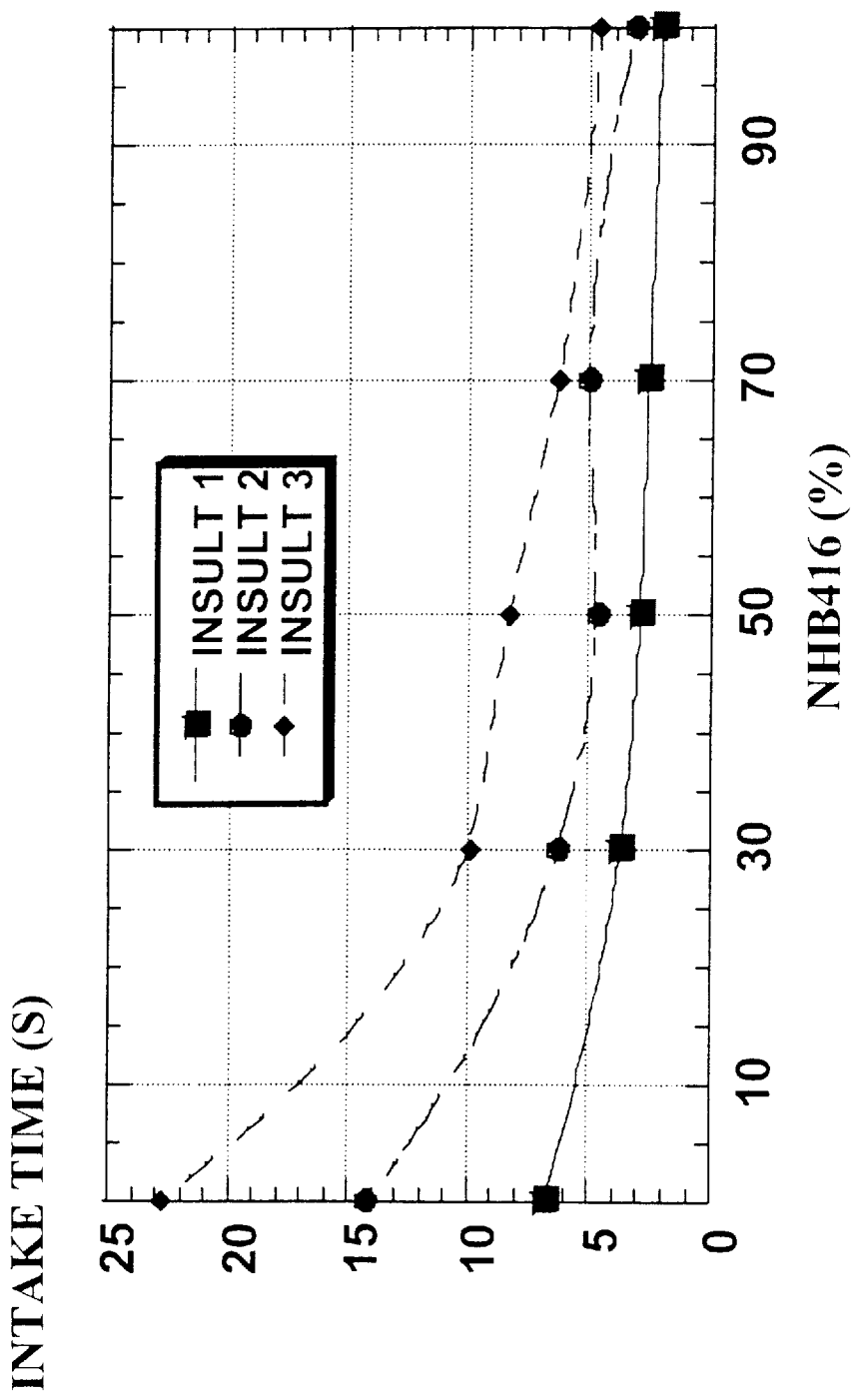
FIG. 3 depicts the relationship between intake time, in seconds, and fiber composition, in weight percent, for different embodiments of the present invention.

The fluid handling properties of wet-formed composites made in accordance with the procedures outlined in Example 1 were measured using a low viscosity menses simulant (see U.S. Pat. No. 5,883,231, entitled "Artificial Menses Fluid," which is incorporated by reference, for recipes of such simulants). For this example, and the examples that follow, the simulant comprised 30% swine red blood cells; 30% swine blood plasma; and 40% bird egg white. Intake times were measured by insulting 0.25 ml of simulant for each insult, at a flow rate of 5 ml/hour, to the surface of a 1-inch by 6-inch sample of the wet-formed composite, and recording the elapsed time at which the applied volume of simulant was no longer detectable visually at the surface of the sample. Three insults were done at the same point to get the intake time for each insult. The results depicted in FIG. 3 are the average of 3 data points. The wet-formed composites used in the test had a basis weight of 600 grams per square meter and contained 5% by dry weight superabsorbent material (Flosorb 60 Lady from Chemtall Inc., Riceboro, Ga.). The superabsorbent had a maximum absorbent capacity of about 300–350 grams of dispersion medium per gram of superabsorbent material. For this example, the dispersion medium was city/municipal water. The superabsorbent material was fully swollen, i.e. the superabsorbent material was at about 95 to about 100% of its maximum absorbent capacity, before the drying step. A calendering device was used to densify the wet-formed composites to a density of 0.3 grams per cubic centimeter and a caliper of 0.217 cm prior to testing. The slurry of fibers comprised various blends of a predominantly bleached, softwood kraft pulp such as CR54 or CR1654 (Alliance Corp.) and NHB416, a crosslinked, resilient fiber from Weyerhaeuser, a business having offices in Federal Way, Wash. Kymene 557LX was added at a level of 0.5 dry weight percent. Superabsorbent material, preswollen as described in Example 1 above, contacted water for about 60 seconds in the mold while making the handsheet. FIG. 3 depicts results of intake time versus varying content of the resilient fiber (NHB416). The results also show that intake time can be adjusted to the desired value by varying the fiber blend.

EXAMPLE 3

Figure 4:
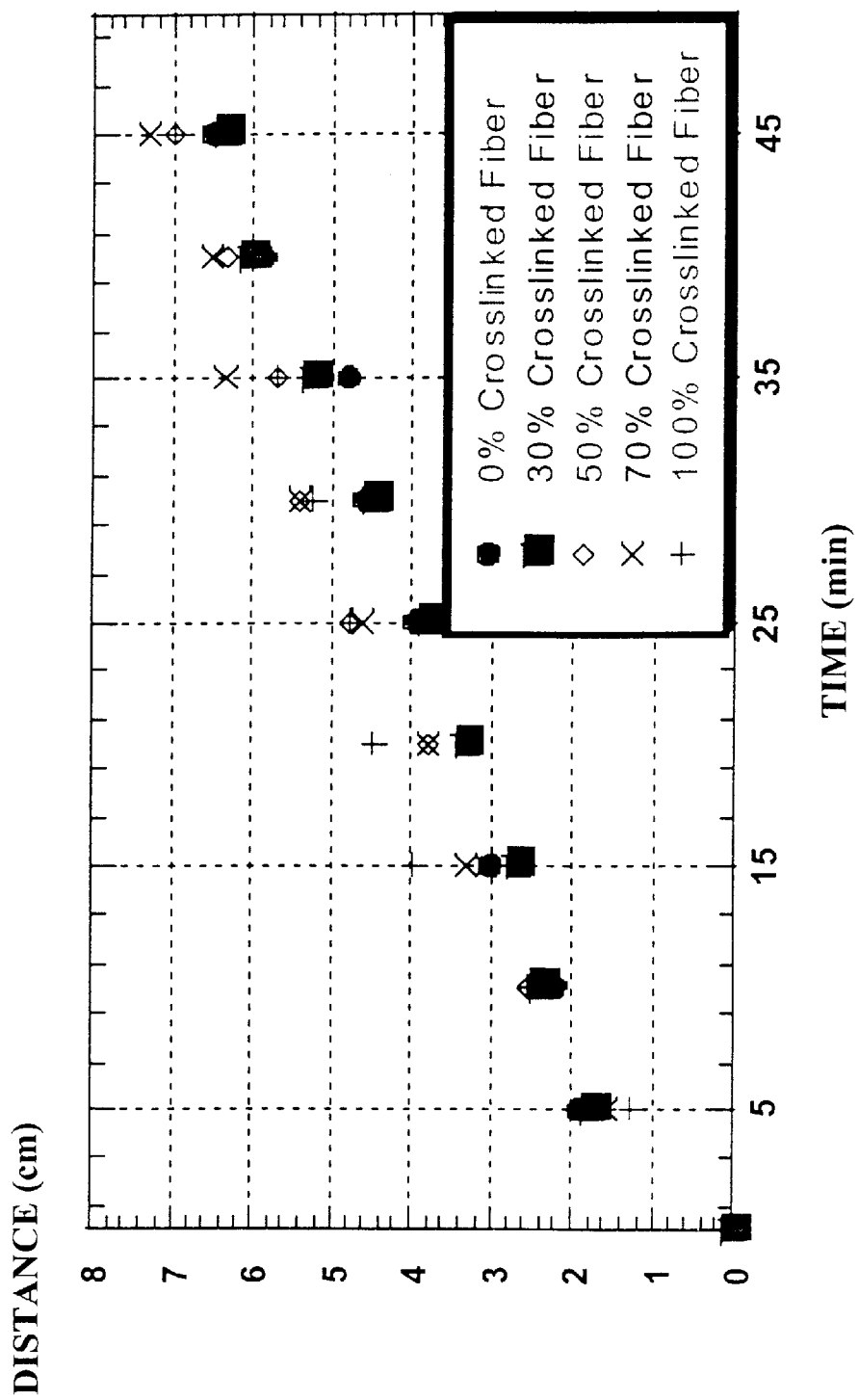
FIG. 4 depicts the relationship between wicking distance, in centimeters, and time, in minutes, for different embodiments of the present invention.

The fluid distribution properties of wet-formed composites prepared as described in Example 1, and having the characteristics of composites used in Example 2, were evaluated using a horizontal wicking test. The test was conducted by applying 5 ml of simulant at the rate of 5 ml/hour using a syringe pump to the center of 1-inch by 6-inch strips of the wet-formed composites. (Note: because of differences in how the simulant was applied between Example 2 and Example 3—i.e., multiple insults versus the continuous delivery of simulant, the rate of decrease of density and the rate of increase in caliper differed between the two examples.) The distance wicked as a function of time was monitored and recorded, with the results depicted in FIG. 4. The distance wicked was measured by determining the total length of the stain, from one end to the other end along the 6-inch dimension of the sample, as the simulant was wicked into and through the wet-formed composite. For each of the fiber blends evaluated, FIG. 3 shows that wicking distance increased with time, indicating that fluid was efficiently wicked away from the point of insult. The data indicate that the simulant was wicked from the point of insult at a wicking velocity of about 1.5 mm min$^{-1}$ (i.e., the approximate slope of a straight line fitting the points).

EXAMPLE 4

Figure 5:
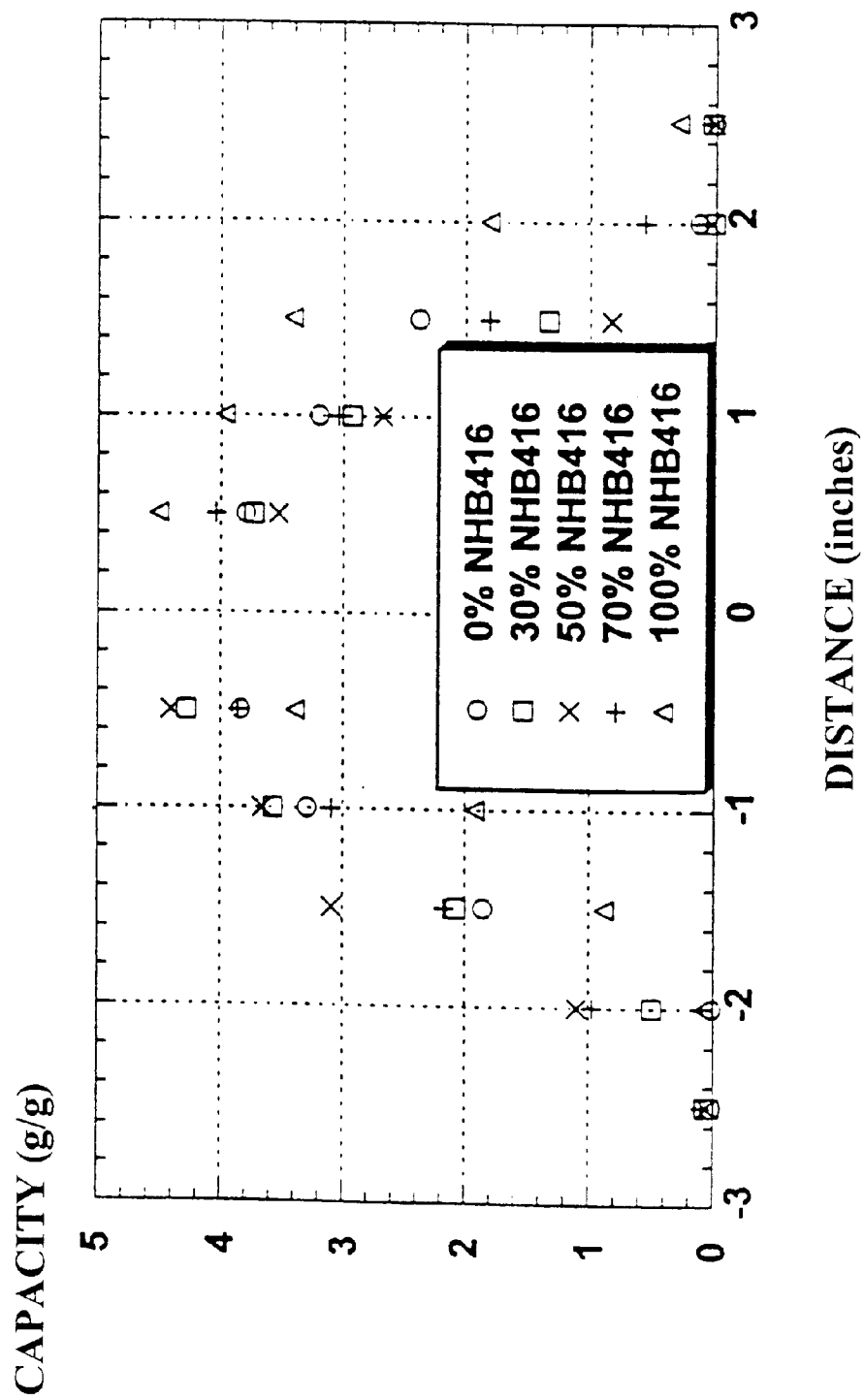
FIG. 5 depicts the relationship between capacity, in grams per gram, and distance from the initial point of fluid insult, in inches, for different embodiments of the present invention.
Figure 6:
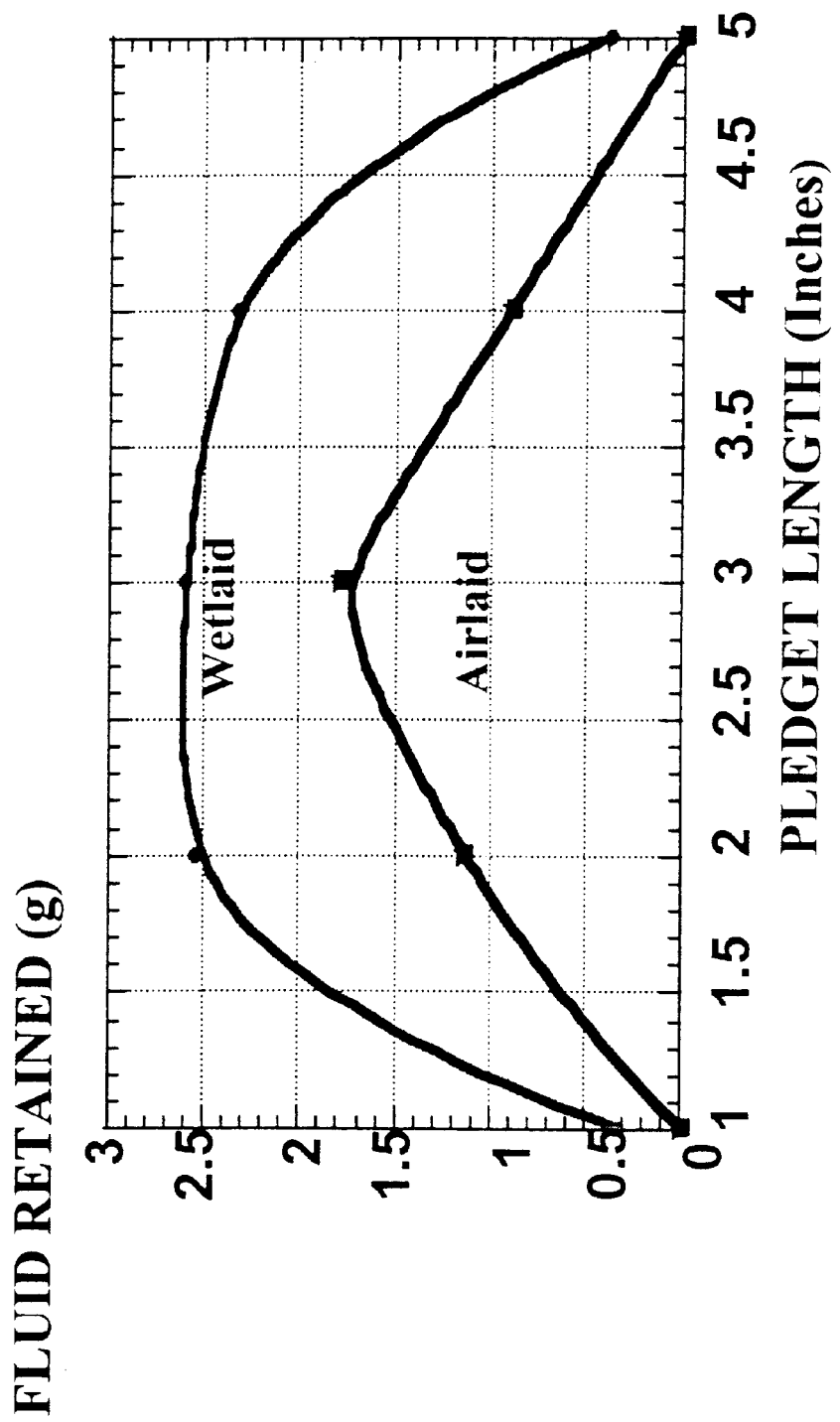
FIG. 6 depicts the relationship between fluid retained, in grams, and pledget length, in inches, for different embodiments of the present invention.

The distribution of fluid in wet-formed composites prepared as described in Example 3 was measured as a function of distance from the point of insult. Samples that had been used to determine wicking distance as described in Example 3 were sectioned so that each section corresponded to a given distance from the initial point of insult. Capacity, in grams per gram, was measured for each section. FIG. 5 depicts the results of this test.

EXAMPLE 5

Figure 7:
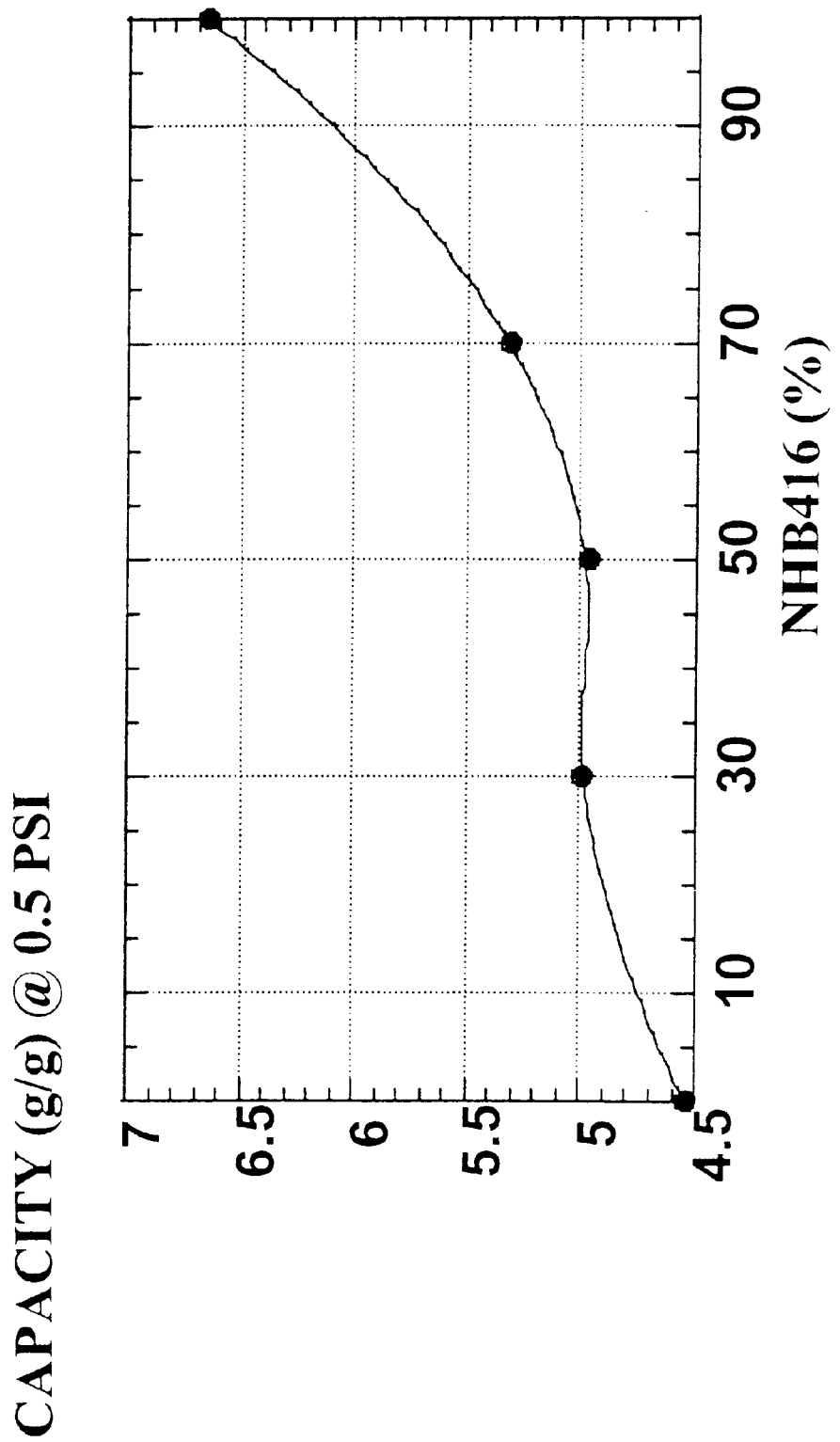
FIG. 7 depicts the relationship between fluid capacity, in grams per gram at a pressure of 0.5 pounds-force per square inch (psi), and fiber composition, in weight percent, for different embodiments of the present invention.

A test that measures the combination of desorption and distribution of simulant by the wet-formed composites prepared as described in Example 1 was conducted by placing a 175 gram per square meter airlaid material (comprising 10% by weight thermoplastic binder fiber T-255, Hoescht-Celanese, and 90% by weight fluff pulp NB416, Weyerhaeuser; the airlaid material having a density of 0.08 gram per cubic centimeter) over a 600 gram per square meter wet-formed composite having a density of 0.3 grams per cubic centimeter and containing 5% by dry weight Flosorb 60 Lady superabsorbent material. The fiber furnish for the wet-formed composite was a blend of 30% NHB 416 and 70% predominantly bleached, softwood kraft pulp, such as CR54 or CR1654. Kymene 557LX was added at a level of 0.5 dry weight percent. A 1-inch by 5-inch strip of the airlaid material was placed on the 1-inch by 5-inch strip of the wet-formed composite and simulant applied to the airlaid strip at a rate of 12 ml/hour using a syringe pump for 45 minutes. At the end of the test the two strips were separated and the fluid distribution in both layers was determined. The results shown in FIG. 7 show the ability of the wet-formed composite to desorb fluid from the airlaid material and distribute/retain the fluid.

EXAMPLE 6

The ability of wet-formed composites prepared as described in Example 1, and having the characteristics of composites used in Example 2, to retain the simulant was measured by allowing a 1.5-inch by 1.5-inch sample of the wet-formed composite to swell in 20 milliliters of simulant in a weight dish for 30 minutes. The sample was then removed from the weight dish and free fluid allowed to drip for 5 seconds. The sample was then placed between two blotter paper sheets (3-inch by 3-inch blotter) and placed between a bladder. The sample between the two blotter paper sheets was then exposed to a pressure of 0.5 pounds-force per square inch (psi) for 30 seconds. The sample was then removed and weighed to determine the absorption capacity under 0.5 psi pressure. The results of retention capacity of the wet-formed composites under 0.5 psi pressure are depicted in FIG. 7.

EXAMPLE 7

Wet-formed composites were prepared and immersed in simulant as described in Example 6. But instead of determining the retention capacity under pressure, the caliper of these wetted wet-formed composites was determined. Upon being wetted with simulant as described in Example 6, the caliper of the wet-formed composite increased to 0.64 cm. Prior to being wetted the wet-formed composite had a caliper of 0.217 cm. Prior to densification, the wet-formed composite had a caliper of 0.665 cm. Thus the caliper of the densified wet-formed composite increased by 195% upon wetting. Caliper was measured under a pressure of 0.05 psig using a Starret-type bulk tester (described below).

EXAMPLE 8

The process generally depicted in FIG. 2 and described above was used to make wet-formed composites. In one case the composite was hydraulically entangled. In a second case the composite was not hydraulically entangled. The forming surface (i.e., a Formtech 90BH Flat Warp 90×50 mesh, single-layer weave, available from Albany International of Portland, Tenn.) and hydraulic-entangling surface (i.e., a 12-C Flat Warp 14×15 mesh, single-layer weave, available from Albany International of Portland, Tenn.) identified above were used to make examples of the present invention. For these examples, the line speed of the papermaking machine was between 9 and 15 feet per minute. The through-air dryer temperature was set to approximately 400 degrees Fahrenheit. The pulp slurry used to make the wet-formed composite was made up by mixing 26 lb of NHB 416, a crosslinked, resilient southern softwood fiber available from Weyerhaeuser, a business having offices in Federal Way, Washington; 54 lb of CR1654, a southern softwood/hardwood blend available from U.S. Alliance, a business having offices in Coosa, Ala.; in 7642 gallons (i.e., about 63,800 lb) of water. The resulting pulp slurry had a consistency of about 0.125%. After the slurry had been made substantially uniform through the action of a mixer, 1.6 lb of a polyacrylate superabsorbent material available under the trade designation Flosorb 60 Lady was added to the pulp slurry in the stock chest. This amount of superabsorbent material corresponded to about 2 dry weight percent, based on total dry weight of the fibers and superabsorbent material present in the wet-formed composite.

The polyacrylate superabsorbent was swellable in the chosen dispersion medium (i.e., water). The superabsorbent material was mixed with the fiber/water slurry for at least about 15 minutes before activating a pump (not shown) to conduct the fiber/superabsorbent/water slurry to the headbox and onto the forming surface. The superabsorbent material was estimated to have absorbed at least about 300 times its weight in the dispersion medium (i.e., water) before the pump was activated. In other words, the superabsorbent material, Flosorb 60 Lady swelled to at least about 85–100% of its maximum absorbent capacity before the pump was activated.

For wet-formed composite that was not hydroentangled, the hydraulic jets were not activated. The foraminous surface passed through the unactivated hydraulic entangling equipment, thereby conducting the wet-formed composite from the forming section to the non-compressive drying section, in this case a through-air drier.

The dried roll of wet-formed composite was later used as a source of smaller samples that were densified as described in Example 1 (i.e., using a Carver-type hydraulic press). The densified wet-formed composite was tested for basis weight, caliper, cohesion, and Gurley Stiffness. The methods by which these characteristics were measured are described below.

A hydraulically entangled wet-formed composite was made in the same way as the composite described in the preceding paragraphs, but in this case the hydraulic entangling equipment was activated. For this example, the jets were operated at a gauge pressure of 600 psig. The specifications for the equipment are generally given above in the description of the process depicted in FIG. 2. Three manifolds produced by Honeycomb Systems, Inc. of Biddeford, Me. were used. Each manifold contained a single row of aligned holes (30 holes per inch/12 holes per centimeter) with each hole having a diameter of 0.007 inches (0.18 millimeters).

After drying, the samples from the roll of hydraulically-entangled composite were densified as described above (again using the Carver-type hydraulic press). The hydraulically entangled wet-formed composite was then tested for basis weight, caliper, cohesion, and Gurley Stiffness.

Table 1 presents a comparison of the physical properties of a hydraulically entangled wet-formed composite (i.e., a wet-formed composite with HET) and a wet-formed composite that was not hydraulically entangled (i.e., a wet-formed composite without HET).

TABLE 1

|  | Basis Weight [g m$^{-2}$] | Caliper [mm] | Cohesion [kg$_f$] | MD Gurley Stiffness [mg$_f$] | CD Gurley Stiffness [mg$_f$] |
| --- | --- | --- | --- | --- | --- |
| Wet-formed composite without HET | 212 | 1.85 | 2.02 | 2131 | 1834 |
| Wet-formed composite with HET | 202 | 1.94 | 5.77 | 1343 | 462 |

The data shows that the hydraulically-entangled wet-formed composite has greater cohesion, and is less stiff, than a wet-formed composite that is not hydraulically entangled.

The above physical characteristics were measured in the following manner. For basis weight, a sample having an area of no less than 20 in$^2$ was placed on a calibrated balance. After the weight of the sample was measured, basis weight was calculated by dividing the weight of the sample by the area of the sample. For this example, the basis weight was determined in an unconditioned room having a temperature of about 68 to about 72 degrees Fahrenheit and a relative humidity of about 60%.

Caliper is a measure of thickness and was measured at 0.05 psi with a Starret-type bulk tester, in units of millimeters. The foot of the bulk tester used in these studies was a small acrylic cylinder measuring about 3 inches wide by about 0.5 inches in thickness.

Internal Cohesion was measured in the following manner. A 2×2 inch sample of material to be tested was adhered with double-sided adhesive to a 2×2 inch metal platen (#1) to which was attached a piston. A fixed, flat platen (#2) is rotated into position above the platen #1 and the platen #1 is pressed against the platen #2 for 3 seconds to secure the sample to the platen #1. The platen #2 is then rotated out of the test area. A 1×1 inch platen (#3) having a piece of double-sided adhesive mounted thereon is rotated into position above the platen #1 and the platen #1 is raised and pressed against the platen #3 for 10 seconds, adhering the sample to the two pieces of double-sided adhesive. The platen #1 is then slowly lowered. A digital force gauge, model DFI50 (available from S. A. Meier Co., Milwaukee, Wis.) is mounted on top of the platen #3. The gauge measures the peak load in kilograms needed to totally separate the sample from the double-sided adhesive. Another description of the internal cohesion test is given in U.S. Pat. No. 5,964,973 to Heath et al. beginning at line 59 in column 14, which is hereby incorporated by reference in a manner consistent herewith. For the test results reported in Table 1, the internal cohesion values are reported for dry samples, hence the values represent dry internal cohesion values.

For purposes of the present invention, the various rigidity stiffness values are determined with respect to a bending moment produced by a force that is directed perpendicular to the plane substantially defined by the length and width of the component being tested. A suitable technique for determining the rigidity, stiffness values described herein is a Gurley Stiffness test, a description of which is set forth in TAPPI Standard Test T 543pm-84 (Stiffness of paper (Gurley type stiffness tester)). A suitable testing apparatus is a Gurley Digital Stiffness Tester; Model 4171-D manufactured by Teledyne Gurley (514 Fulton Street, Troy, N.Y. 12181–0088). This instrument allows the testing of a wide variety of materials through the use of various lengths and widths in combination with the use of a 5, 25, 50, or 200 gram weight placed in one of three positions on the pointer of the apparatus. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample and are expressed in terms of milligrams. The standard size sample has a width of 1" and a nominal length of 3" (actual length of 3.5"). The actual length of the sample is the nominal length, plus an additional 0.25" of length for holding in the clamp and another 0.25" of length for overlapping the vane. Tables of factors for taking scale readings generated with non-standard sized test samples and converting the readings to the stiffness of the standard size sample are given in the Instruction Manual for the Gurley Stiffness Tester provided by Teledyne Gurley. Accordingly, other designated dimensions for the test sample may also be conveniently employed, so long as the appropriate conversion factor is employed to determine the appropriate value which corresponds to the standard size sample.

EXAMPLE 9

The process generally depicted in FIG. 2 and described (see Example 8) was used to make wet-formed composites. In two cases the composite was hydraulically entangled at a gauge pressure of either 600 psig or 1000 psig. In a third case the composite was not hydraulically entangled. The forming surface and hydraulic-entangling surface identified above were used to make examples of the present invention. For these examples, the line speed of the papermaking machine was 9 feet per minute. The through-air dryer temperature was set to approximately 400 degrees Fahrenheit. The pulp slurry used to make the wet-formed composite was made up by mixing 26 lb of NHB 416, a resilient, crosslinked southern softwood fiber available from Weyerhaeuser, a business having offices in Federal Way, Wash.; 54 lb of CR1654, a southern softwood/hardwood blend available from U.S. Alliance, a business having offices in Coosa, Ala.; in 63,800 lb of water. The resulting pulp slurry had a consistency of about 0.125%. After the slurry had been made substantially uniform through the action of a mixer, 1.6 lb of a polyacrylate superabsorbent material available under the trade designation Flosorb 60 Lady was added to the pulp slurry in the stock chest. This amount of superabsorbent material corresponded to 2 dry weight percent, based on total dry weight of the fibers and superabsorbent material present in the wet-formed composite.

The polyacrylate superabsorbent was swellable in the chosen dispersion medium (i.e., water). The superabsorbent material was mixed with the fiber/water slurry for at least about 15 minutes before activating a pump (not shown) to conduct the fiber/superabsorbent/water slurry to the headbox and onto the forming surface. The superabsorbent material was estimated to have absorbed at least about 300 times its weight in the dispersion medium (i.e., water) before the pump was activated.

For wet-formed composite that was not hydroentangled, the hydraulic jets were not activated. The foraminous surface passed through the unactivated hydraulic entangling equipment, thereby conducting the wet-formed composite from the forming section to the non-compressive drying section, in this case a through-air drier.

After passing through unactivated hydroentangling equipment, the dryness (i.e., the percent solids) of the wet-formed composite was determined.

A hydraulically entangled wet-formed composite was made in the same way as the composite described in the preceding paragraphs, but here the hydraulic entangling equipment was activated. For this example, the hydraulic entangling equipment comprised three manifolds produced by Honeycomb Systems, Inc. of Biddeford, Me., each manifold containing a single row of aligned holes (30 holes per inch/12 holes per centimeter) with each hole having a diameter of 0.007 inches (0.18 millimeters). The jets were operated at a gauge pressure of either 600 psig or 1000 psig.

After passing through activated hydroentangling equipment, the dryness (i.e., the percent solids) of the wet-formed composite was determined.

Table 2 presents a comparison of the dryness (i.e., percent solids) of the wet-formed composite with and without hydraulic entangling of the composite's constituent fibers.

TABLE 2

| Hydroentangling? | No | Yes | Yes |
|---|---|---|---|
| HET Gauge Pressure [psig] | 0 | 600 | 1000 |
| Dryness [% solids] | 20.6 | 26.5 | 35.5 |

As can be seen from Table 2, activation of the hydraulic entangling equipment increased the dryness of the wet-formed composite. Furthermore, increasing the gauge pressure of the jets while hydroentangling increased the dryness of the hydroentangled wet-formed composite.

Although the present invention has been described in considerable detail with reference to certain versions, other versions are possible. The spirit and scope of the appended claims should not be limited to the description of specific versions contained herein.

What is claimed is:

1. A wet-formed composite having latent voids and macro-cavities, the wet-formed composite comprising interbonded fibers defining a plurality of latent voids and macro-cavities between the fibers, the fibers including at least about 10% resilient fibers; and superabsorbent material contained by the interbonded fibers, the superabsorbent material present in an amount of less than about 5 dry weight percent, but more than 0, based on the total dry weight of the fibers and superabsorbent material;

said wet-formed composite having a density of about 0.06 grams per cubic centimeter or greater and a basis weight greater than about 100 grams per square meter.

2. The wet-formed composite of claim 1 wherein the superabsorbent material is present in an amount of about 2 dry weight percent or less, but more 0, based on the total weight of the superabsorbent material and fiber.

3. The wet-formed composite of claim 1 further comprising a wet-strength additive.

4. The wet-formed composite of claim 3 wherein the wet:dry cohesive strength ratio is about 0.1 or greater.

5. The wet-formed composite of claim 3, wherein at least about 30% of the fibers are resilient fibers, the dry internal-cohesion value is greater than about 5 $kg_f$, and the cross-directional Gurley-type stiffness value is less than about 500 $mg_f$.

6. The wet-formed composite of claim 4, wherein the intake-time value is less than about 20 seconds.

7. The wet-formed composite of claim 3, wherein at least about 30% of the fibers are resilient fibers and the intake-time value is less than about 15 seconds.

8. The wet-formed composite of claim 3, wherein at least about 30% of the fibers are resilient fibers and the wicking-velocity value is about 1.5 millimeters per minute.

9. The wet-formed composite of claim 3, wherein at least about 30% of the fibers are resilient fibers and the caliper of the composite increases by at least about 100% when wetted.

10. A method of making a wet-formed composite having latent voids and macro-cavities, the method comprising providing fibers;

providing a dispersion medium for the fibers providing superabsorbent material, swellable in the dispersion medium, in an amount of less than about 5 dry weight percent, based on the total dry weight of the fibers and superabsorbent material;

thereafter combining the fibers, superabsorbent material, and dispersion medium;

forming a wet-formed composite, comprising fibers and superabsorbent material and defining voids between the fibers, from the combination of fibers, superabsorbent material, and dispersion medium;

providing sufficient contact time between the superabsorbent material and dispersion medium so that the superabsorbent material absorbs at least about 20 times or greater its dry weight of dispersion medium prior to drying the wet-formed composite;

drying the wet-formed composite so that the superabsorbent material shrinks, thereby forming macro-cavities between the fibers; and densifying the wet-formed composite to collapse the voids and macro-cavities, thereby forming latent voids and macro-cavities within the densified wet-formed composite;

wherein the densified wet-formed composite has a density of about 0.06 grams per cubic centimeter or greater and a basis weight greater than about 100 grams per square meter.

11. The method of claim 10, wherein the superabsorbent material is present in an amount of about 2 dry weight percent or less, based on the total weight of the superabsorbent material and fiber.

12. The method of claim 10, wherein the superabsorbent material in the wet-formed composite swells to about 85 percent or more of its maximum absorbent capacity in the dispersion medium before the wet-formed composite is dried.

13. The method of claim 10 wherein the superabsorbent material in the wet-formed composite swells to about 95 percent or more of its maximum absorbent capacity in the dispersion medium before the wet-formed composite is dried.

14. The method of claim 12, wherein the superabsorbent material shrinks during drying to about 5 percent or less of its maximum absorbent capacity in the dispersion medium.

15. The method of claim 12, wherein the superabsorbent material shrinks during drying to about 2 percent or less of its maximum absorbent capacity in the dispersion medium.

16. The method of claim 14, wherein the fibers comprise resilient fibers.

17. The method of claim 16, further comprising the steps of:

providing a wet-strength additive;

adding the wet-strength additive to the fibers, dispersion medium, superabsorbent material, or a combination comprising two or more of fibers, dispersion medium, and superabsorbent material.

18. The method of claim 10, further comprising the step of hydraulically entangling fibers.

* * * * *